(12) United States Patent  (10) Patent No.: US 8,967,026 B2
Walter  (45) Date of Patent: Mar. 3, 2015

(54) MICROTOME HAVING AN AUTO-ROCKING MODE

(71) Applicant: Leica Biosystems Nussloch GmbH, Nussloch (DE)

(72) Inventor: Roland Walter, Reilingen (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 59 days.

(21) Appl. No.: 13/926,643

(22) Filed: Jun. 25, 2013

(65) Prior Publication Data

US 2014/0026728 A1 Jan. 30, 2014

(30) Foreign Application Priority Data

Jul. 27, 2012 (DE) .......................... 10 2012 106 845

(51) Int. Cl.
*B26D 5/08* (2006.01)

(52) U.S. Cl.
USPC ............................... 83/248; 83/530; 83/915.5

(58) Field of Classification Search
USPC ......................................... 83/915.5, 530, 248
See application file for complete search history.

(56) References Cited

U.S. PATENT DOCUMENTS

| | | | | |
|---|---|---|---|---|
| 3,440,913 A | * | 4/1969 | Persidsky et al. | 83/422 |
| 3,785,234 A | * | 1/1974 | Sitte | 83/414 |
| 4,495,844 A | * | 1/1985 | Jackson et al. | 83/715 |
| 5,123,789 A | * | 6/1992 | Ohtani et al. | 408/1 R |
| 5,181,443 A | * | 1/1993 | Sitte et al. | 83/72 |
| 5,761,977 A | * | 6/1998 | Jakobi et al. | 83/13 |
| 8,635,934 B2 | * | 1/2014 | Kong et al. | 83/42 |
| 2004/0197897 A1 | * | 10/2004 | Leighton | 435/286.2 |
| 2013/0186248 A1 | * | 7/2013 | Heid | 83/530 |

FOREIGN PATENT DOCUMENTS

| | | |
|---|---|---|
| DE | 102 58 553 B4 | 7/2004 |
| DE | 10 2007 023 457 A1 | 11/2008 |
| DE | 102008016165 A1 | 10/2009 |
| DE | 102008031137 A1 * | 1/2010 |
| EP | 1 037 032 B1 | 8/2008 |
| WO | 2012/041284 A1 | 4/2012 |

OTHER PUBLICATIONS

United Kingdom Intellectual Property Office, Search Report dated Sep. 16, 2013 in corresponding British Patent Application No. GB1307826.6.

* cited by examiner

*Primary Examiner* — Sean Michalski
(74) *Attorney, Agent, or Firm* — Hodgson Russ LLP

(57) ABSTRACT

The present invention relates to a microtome (10) including a sample holder (12) a cutting unit (16), and a drive unit (22) capable of producing a relative movement between the sample holder (12) and the cutting unit (16) for cutting the sample. In addition, the microtome (10) has a handwheel (32) and an encoder (38). A control unit (40) controls the drive unit (22) as a function of the rotational movement of the handwheel (32) detected by the encoder (38) and in such a way that, in a first operating mode, the relative movement produced between the sample holder (12) and the cutting element (16) by the drive unit (22) when the handwheel (32) is rotated through a full revolution has a maximum first stroke length and that, in a second operating mode, the relative movement has a preset second stroke length shorter than the maximum first stroke length.

15 Claims, 3 Drawing Sheets

MICROTOME HAVING AN AUTO-ROCKING MODE

CROSS REFERENCE TO RELATED APPLICATIONS

This application claims priority of German patent application number 10 2012 106 845.3 filed Jul. 27, 2012, the entire disclosure of which is incorporated by reference herein.

FIELD OF THE INVENTION

The present invention relates to a microtome for cutting thin sections, including a sample holder for receiving a sample to be microtomed, a cutting unit for cutting the sample, and a drive unit for producing a relative movement between the sample holder and the cutting unit for cutting the sample. The microtome further has a manually operable handwheel and an encoder which detects rotational movement of the handwheel. A control unit controls the drive unit as a function of the rotational movement of the handwheel detected by the encoder.

Microtomes are used to cut thin sections from samples. These sections are subsequently placed on a coverslip, suitably processed, and then examined under a microscope. The samples are, in particular, tissue samples which are embedded in a paraffin block prior to cutting.

Microtomes are known where the handwheel is mechanically connected to the sample holder or to the cutting unit, so that rotation of the handwheel causes the sample holder or the cutting unit to move relative to the respective other device, thus producing a reciprocating movement resulting in the cutting of the sample. The mechanical coupling may be provided, for example, by a crank mechanism and is generally designed such that a full revolution of the handwheel produces exactly one reciprocating movement, so that exactly one thin section is cut when the handwheel is rotated through one full revolution. Depending on the sample used, its size, and the desired section quality, it is frequently not necessary to perform the reciprocating movement through the full stroke length. In this case, the handwheel is moved by the user only up to a certain position, from where it is turned back in the opposite direction of rotation to its initial position. Such a movement is accordingly referred to as "rocking movement" or "rocking". Compared to a purely rotational movement in one direction of rotation, such rocking movements are unergonomic for the user and, therefore, become uncomfortable over time.

Also known are microtomes in which the relative movement between the sample holder and the cutting unit is accomplished solely by motor means. These microtomes have the problem that it is impossible or difficult for the user to influence the cutting movement itself, for example, when working with sensitive samples.

Document EP 1037032 B1 describes a microtome including a handwheel whose rotational movements are detected by an angle encoder. A motor moves the sample holder relative to the cutting unit according to the detected rotational movement. Thus, although no mechanical coupling exists between the handwheel and the sample holder or the cutting element, the movement effected by the motor is nevertheless performed in the same manner as if such mechanical coupling existed. Thus, the user of such a microtome must move the handwheel in a rocking manner when he or she wishes to use a shorter stroke.

Documents DE 10 2007 023 457 A1 and DE 102 58 553 B4 describe microtomes in which the position of the cutting window within the reciprocating movement is automatically adapted to the sample to be cut.

SUMMARY OF THE INVENTION

It is an object of the present invention to provide a microtome which enables easy setting of the cutting speed and section quality.

This object is achieved by a microtome having the features of claim 1. Advantageous refinements are recited in the dependent claims.

In accordance with the present invention, two operating modes are provided, the control unit controlling the drive unit such that in a first operating mode, the relative movement produced between the sample holder and the cutting element by the drive unit when the handwheel is rotated through a full revolution has a maximum first stroke length, and that in a second operating mode, the relative movement produced between the sample holder and the cutting element by the drive unit when the handwheel is rotated through a full revolution has a preset second stroke length shorter than the maximum first stroke length.

Thus, in the first operating mode, the drive unit is controlled by the control unit such that the cutting movement is performed in the same manner as if the handwheel where mechanically coupled to the sample holder or to the cutting unit. In contrast, in the second operating mode, the drive unit performs a rocking movement, although no rocking movement is input from the handwheel, but instead a full revolution is performed in one direction of rotation. Thus, in the second operating mode, an ergonomically favorable rotational movement of the handwheel in one direction is converted into a rocking movement, so that regardless of whether the user wants to perform a rocking movement or a "normal" cutting movement with the maximum stroke length, he or she needs to rotate the handwheel only in one direction and, by selecting the operating mode, he or she can select whether to perform the "normal" cutting movement with the maximum stroke length or a rocking movement.

The control unit controls the drive unit such that a full revolution of the handwheel produces exactly one reciprocating movement for cutting a thin section, regardless of the set operating mode and the set stroke length. Accordingly, regardless of the selected settings, exactly one thin section is cut at each full revolution, so that the cutting movement can be easily and intuitively controlled by the user.

Thus, for the same number of strokes; i.e. sections, the rocking movement allows the cutting speed to be reduced due to the shorter distance traveled, thereby improving the section quality. Conversely, for the same section quality, a higher cutting frequency can be achieved, and thus the number of thin sections that can be produced per unit time can be increased. Furthermore, after microtoming of the sample is complete, the sample can be quickly moved to a safe distance from the cutting unit, and can thus be changed in a safe and simple way. To this end, in particular, the first operating mode is selected, so that the complete maximum first stroke length is traversed, which allows rapid movement of the sample.

The second operating mode is also referred to as "auto-rocking mode" because of the rocking movement performed in this mode.

In a preferred embodiment, the sample holder, and thus the sample receivable therein, are moved by the drive unit while the cutting unit is stationary. Alternatively, the sample holder may be stationary and the cutting unit may be moved relative thereto.

The microtome has in particular a setting element for manually setting the operating mode. This allows the user to easily switch between the two operating modes, depending on the sample to be microtomed. The setting element is in particular in the form of a switch, such as, for example, a toggle switch and/or a rotary knob.

In a particularly preferred embodiment, the second stroke length; i.e., the stroke length that is traversed during the rocking movement in the second operating mode, is not fixedly preset, but can instead be selected by the user of the microtome using an operator control. Thus, the stroke length of the rocking movement can be individually adapted to the sample to be microtomed.

In a particularly preferred embodiment, at least two selectable stroke lengths are preset for the second operating mode. Using the operator control, the user can select the one of the preset stroke lengths that is to be used in the second operating mode. In particular, a plurality of preset stroke lengths is provided, which allows easy and accurate adjustment of the stroke length.

Alternatively, the second stroke length may be freely set (i.e. set to any value in a continuous range) between a predetermined minimum stroke length and the maximum first stroke length using the operator control. The predetermined minimum stroke length is, in particular, a stroke length of 0 mm, so that the stroke length may be freely set up to the maximum first stroke length.

The operator control for setting the second stroke length includes, in particular, a rotary knob, a keypad and/or a touch screen. In particular, in the case of a rotary knob, one position of the rotary knob is defined as the minimum stroke length and another position of the rotary knob is defined as the maximum first stroke length. The user can select the desired second stroke length by turning the rotary knob to a position between these two preset defined positions. Alternatively, the setting can be made by entering the desired stroke length via a keypad or a touch screen. In this case, the stroke length may be settable as an absolute value or as a relative value of the maximum first stroke length.

Furthermore, it is advantageous for the control unit to receive from the encoder signals and/or data containing information about the rotational movement of the handwheel and/or to convert these received signals and/or data as a function of the set operating mode into corresponding control data and/or control signals for controlling the drive unit. In particular, in the first operating mode, the control unit converts the signals and/or data such that the cutting movement is performed in the same manner as if there were a mechanical coupling to the handwheel. In contrast, in the second operating mode, the control unit converts the signals and/or data such that the rotational movement of the handwheel in only one direction is converted into a rocking movement.

The drive unit includes in particular an electric motor having an output shaft via which the relative movement between the sample holder and the cutting unit is powered. More specifically, the sample holder is mechanically coupled to the output shaft such that it performs the reciprocating movement relative to the cutting unit.

In the first operating mode, the motor rotates its output shaft in particular continuously in a first direction of rotation, so that the cutting movement performed corresponds to the cutting movement that would be produced in the case of a direct mechanical coupling to the handwheel when the handwheel is rotated in the first direction of rotation.

In contrast, in the second operating mode, the control unit controls the motor such that the output shaft is initially driven in a first direction of rotation, and that after the second stroke length is reached, it is driven in a second direction of rotation opposite to the first direction of rotation. Accordingly, the sample holder, respectively the cutting unit, is initially moved in a first direction until the second stroke length is reached, whereupon it is moved back to its initial position without the full maximum stroke length having been reached.

After the initial stroke position is reached again, the output shaft is in particular driven in the first direction of rotation again, so that the next stroke can be executed.

It is particularly advantageous if in the second operating mode, the control unit controls the motor such that a reversal of direction from the first direction of rotation to the second direction of rotation is effected each time the handwheel reaches a preset first angular position and/or a reversal of direction from the second direction of rotation to the first direction of rotation is effected each time the handwheel reaches a preset second angular position. The angle between the first and second angular positions is in particular 180°. It is particularly advantageous if the first angular position corresponds to the upper position of the handwheel and if the second angular position corresponds to the lower position of the handwheel. The upper position of the handwheel is in particular the position in which a handle of the handwheel is in its topmost position when the microtome is in its operational orientation. Accordingly, the lower position of the handwheel is the position in which the handle is in its lowermost position.

The control unit controls the drive unit in particular such that when the direction of rotation is reversed, the rotation of the drive shaft is accomplished with suitable starting ramps.

BRIEF DESCRIPTION OF THE DRAWING VIEWS

Further features and advantages of the present invention will become apparent from the following description of exemplary embodiments thereof, taken in conjunction with the accompanying drawings, in which.

DETAILED DESCRIPTION OF THE INVENTION

Figure 1:
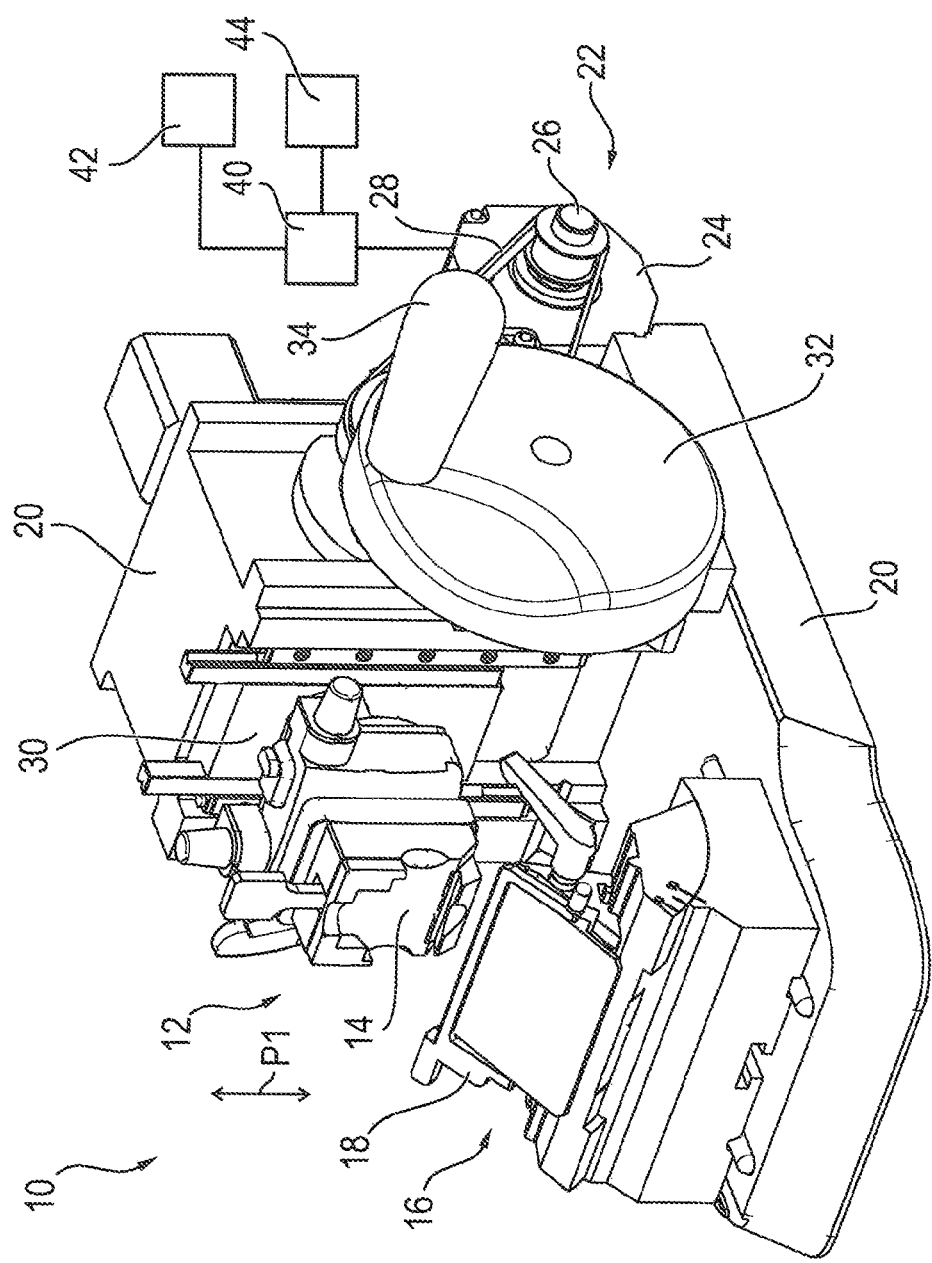
FIG. 1 is a schematic perspective view of a microtome.
Figure 2:
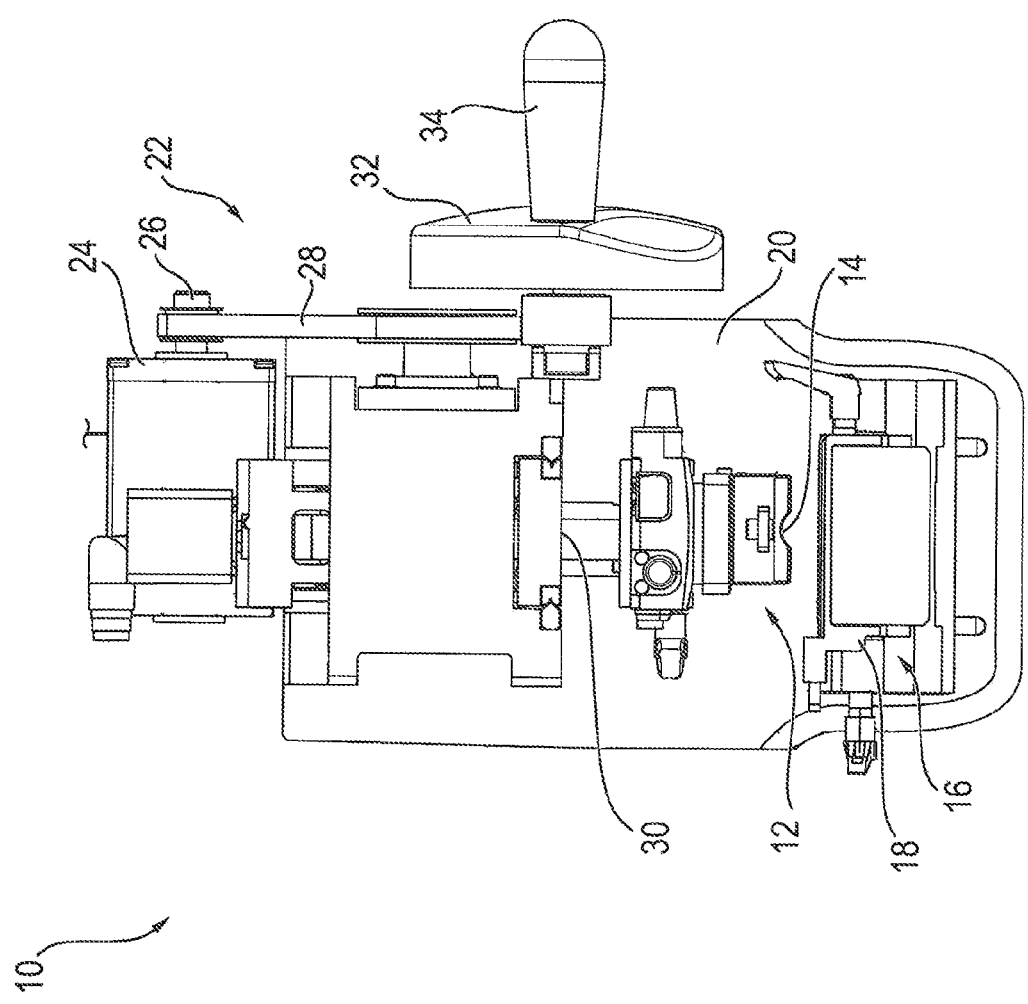
FIG. 2 is a top view of the microtome of FIG. 1.

FIG. 1 shows a microtome 10 in schematic perspective view. The housing of microtome 10 has been omitted here to allow better viewing of the interior components. FIG. 2 shows a top view of the microtome of FIG. 1.

Microtome 10 includes a sample holder 12 in which the sample to be microtomed (e.g., a tissue sample) can be clamped by means of a chuck 14.

Microtome 10 further has a cutting unit 16 which, in the exemplary embodiment shown in FIG. 1, is in the form of a blade holder 18 capable of holding a blade or knife.

Cutting unit 16 is stationary relative to microtome frame 20, whereas sample holder 12 is movable relative to cutting unit 16 by a drive unit 22 in the direction of double-headed arrow P1 in a reciprocating manner, so that the sample received in sample holder 12 is cut by cutting unit 16 as a result of this reciprocating movement.

Drive unit 22 includes a motor 24 whose output shaft 26 is connected by a toothed belt 28 to a coupling mechanism 30 via which sample holder 12 in turn is moved relative to cutting unit 16.

Figure 4:
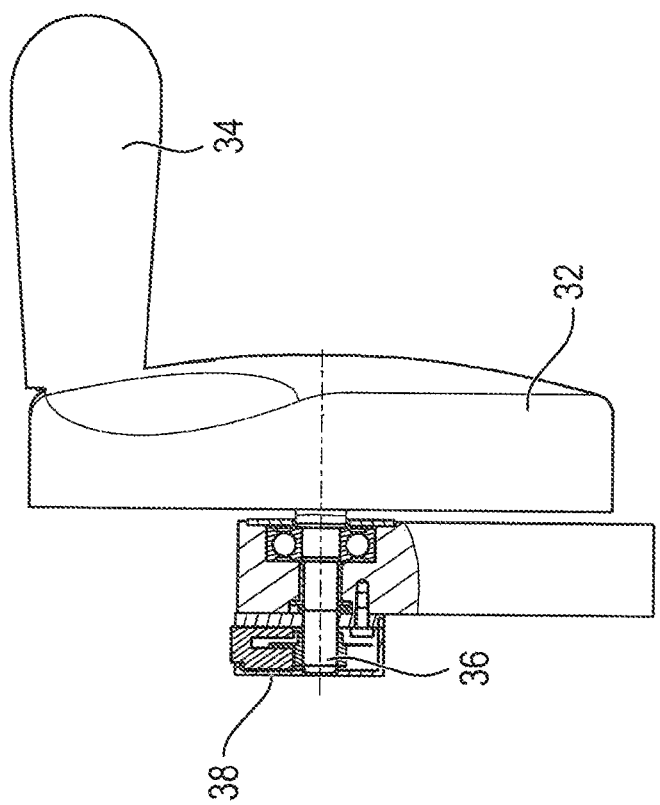
FIG. 4 is a partially sectional side view of the handwheel shown in FIG. 3.
Figure 3:
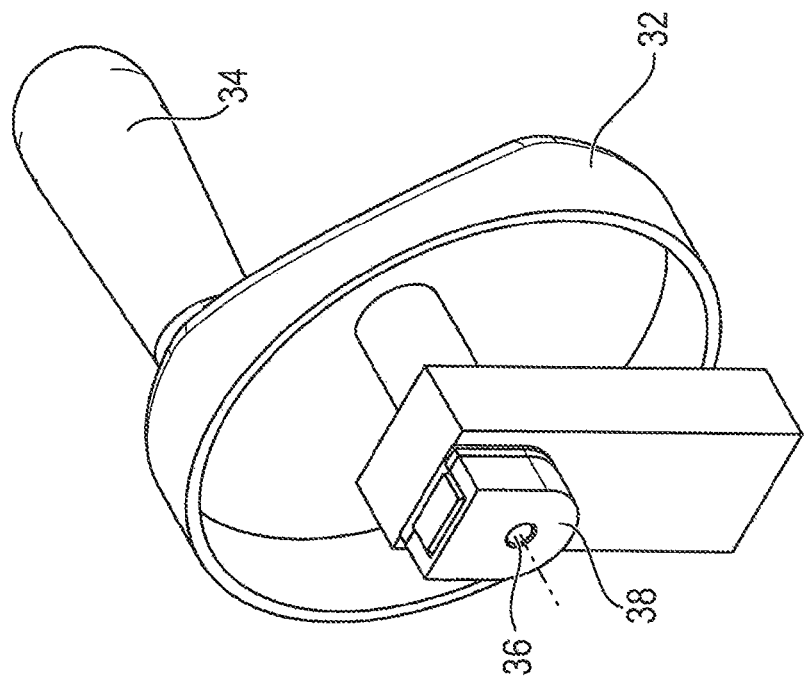
FIG. 3 is a schematic perspective view of the handwheel of the microtome shown in FIGS. 1 and 2.

Moreover, microtome 10 includes a handwheel 32 which has a handle 34 and can be operated manually by the user of microtome 10. FIG. 3 shows this handwheel in schematic perspective view. FIG. 4 shows handwheel 32 in partially cross-sectional side view.

Handwheel 32 is mounted on a shaft 36. This shaft is not coupled to drive unit 22 for moving sample holder 12. Instead, an encoder 38, in particular a rotary encoder, is used to detect rotational movement of shaft 36, and thus rotational movement of handwheel 32. The signals and/or data generated by encoder 38 as a function of the detected rotational movement of handwheel 32 are transmitted to a control unit 40 which converts the received data and/or signals into control data and/or control signals for controlling motor 24.

In a first operating mode of microtome 10, control unit 40 converts the received data and/or signals into the control data or control signals in such a way that when handwheel 32 is rotated through a full revolution, sample holder 12 performs a full reciprocating movement with a maximum first stroke length. Thus, in the first operating mode, motor 24 is driven by control unit 40 such that it effects the relative movement between sample holder 12 and cutting unit 16 in the same manner as if there were a direct mechanical coupling between handwheel 32 and sample holder 12.

In contrast, in a second operating mode, called "auto-rocking mode", control unit 40 converts the data and/or signals received from encoder 38 into the control data and/or control signals for drive unit 22 in such a way that when handwheel 32 is rotated through a full revolution, a so-called rocking movement is performed with a second stroke length shorter than the maximum first stroke length. During such rocking movement, sample holder 12 is not moved through the full maximum first stroke length relative to cutting unit 16. Instead, it is only moved until the second stroke length is reached, whereupon it is moved back to its initial position.

To this end, control unit 40 controls motor 24 in particular such that output shaft 26 is driven in a first direction of rotation until the second stroke length is reached, and that after the second stroke length is reached, it is driven in a second direction of rotation opposite to the first direction of rotation. Consequently, sample holder 12 is also initially moved in a first direction and then in a second direction opposite to the first direction.

Motor 24 is controlled in particular such that the direction of rotation of output shaft 26 is reversed each time handwheel 32 is in an upper position or in a lower position; the upper position being the position in which handle 34 is in the top position, as is shown in FIGS. 1 through 4. In contrast, the lower position is the position in which handle 34 is in its lowermost position; i.e., the position in which handwheel 32 is in a position rotated 180° from its position shown in FIGS. 1 through 4.

This allows the user to always perform an ergonomically favorable full rotation in only one direction, while at the same time allowing a rocking movement to be performed when the second operating mode is activated. The rocking movement may be used to adapt the stroke length to the sample to be microtomed. Thus, for the same number of strokes per minute, the cutting speed can be reduced due to the shorter stroke length, thereby achieving better section quality. Conversely, for a constant section quality, a higher cutting frequency can be achieved, so that a larger number of thin sections can be produced per minute.

Microtome 10 further includes a setting element 42 which allows the user of microtome 10 to select between the first and second operating modes. This setting element is in particular in the form of a switch, such as, for example, a toggle switch, or a knob.

In addition, microtome 10 has an operator control 44 which allows the user of microtome 10 to set the second stroke length. This operator control may be, for example, a rotary knob, a keypad and/or a touch screen. In particular, there may be a plurality of preset second stroke lengths from which the user may select the desired second stroke length for the rocking movement depending on the sample to be microtomed. Alternatively, the second stroke lengths may be freely selected by the user.

Setting element 42 and/or operator control 44 are disposed in particular on the housing of microtome 10, preferably near handwheel 32.

In FIG. 1, the arrangement of control unit 40, setting element 42, and operator control 44 is shown only schematically since, as described above, the housing has been omitted because these devices would otherwise not be visible.

In an alternative embodiment, setting element 42 and/or operator control 44 may not be disposed on microtome 10 itself, but instead, the operating mode and/or the second stroke length may be set using a computer connected to microtome 10 via a data link.

In another alternative embodiment of the present invention, sample holder 12 may be stationary, and cutting unit 16 may be moved by drive unit 22 relative to stationary sample holder 12 when cutting the sample.

What is claimed is:

1. A microtome for cutting thin sections, comprising:
   a sample holder (12) for receiving a sample to be microtomed,
   a cutting unit (16) for cutting the sample,
   a drive unit (22) for producing a relative movement between the sample holder (12) and the cutting unit (16) for cutting the sample,
   a manually operable handwheel (32),
   an encoder (38) for detecting a rotational movement of the handwheel (32), and
   a control unit (40) which controls the drive unit (22) as a function of the rotational movement of the handwheel (32) detected by the encoder (38),
   wherein in a first operating mode, the control unit (40) controls the drive unit (22) such that the relative movement produced between the sample holder (12) and the cutting element (16) by the drive unit when the handwheel (32) is rotated through a full revolution has a maximum first stroke length;
   wherein in a second operating mode, the control unit (40) controls the drive unit (22) such that the relative movement produced between the sample holder (12) and the cutting element (16) by the drive unit when the handwheel (32) is rotated through a full revolution has a preset second stroke length shorter than the maximum first stroke length; and
   wherein the control unit (40) controls the drive unit (22) such that a full revolution of the handwheel (32) produces exactly one single reciprocating movement for cutting a thin section, regardless of the set operating mode and the set stroke length.

2. The microtome (10) as recited in claim 1, wherein the microtome (10) has a setting element (42) for manually setting the operating mode.

3. The microtome (10) as recited in claim 2, wherein setting element (42) includes a switch or a rotary knob.

4. The microtome (10) as recited in claim 1, wherein the second stroke length can be set using an operator control (44).

5. The microtome (10) as recited in claim 4, wherein at least two selectable stroke lengths are defined for the second operating mode, and wherein one of the at least two preset stroke lengths that is to be used as the second stroke length for the second operating mode can be selected using the operator control (44).

6. The microtome (10) as recited in claim 4, wherein the second stroke length can be freely set between a predetermined minimum stroke length and the maximum first stroke length using the operator control (44).

7. The microtome (10) as recited in claim 4, wherein the operator control (44) includes a rotary knob, a keypad and/or a touch screen.

8. The microtome (10) as recited in claim 1, wherein the control unit (40) receives signals and/or data containing information about the rotational movement of the handwheel (32), and wherein the control unit (40) converts the received signals and/or data as a function of the set operating mode into corresponding control data and/or control signals for controlling the drive unit (22).

9. The microtome (10) as recited in claim 1, wherein the drive unit (22) includes an electric motor (24) having an output shaft (26).

10. The microtome (10) as recited in claim 9, wherein in the first operating mode, the motor (24) rotates its output shaft (26) continuously in a first direction of rotation.

11. The microtome (10) as recited in claim 9, wherein in the second operating mode, the control unit (40) controls the motor such that the output shaft (26) is initially driven in a first direction of rotation and, after the second stroke length is reached, it is driven in a second direction of rotation opposite to the first direction of rotation.

12. The microtome (10) as recited in claim 11, wherein in the second operating mode, the control unit (40) controls the motor (24) such that the output shaft (26) is initially driven in a first direction of rotation and, after the second stroke length is reached, it is driven in a second direction of rotation opposite to the first direction of rotation and, after an initial stroke position is reached, it is driven in the first direction of rotation again.

13. The microtome (10) as recited in claim 12, wherein in the second operating mode, the control unit (40) controls the motor (24) such that a reversal of direction from the first direction of rotation to the second direction of rotation is effected each time the handwheel (32) reaches a defined first angular position.

14. The microtome (10) as recited in claim 13, wherein in the second operating mode, the control unit (40) controls the motor (24) such that a reversal of direction from the second direction of rotation to the first direction of rotation is effected each time the handwheel (32) reaches a defined second angular position.

15. The microtome (10) as recited in claim 14, wherein an angle between the first and second angular positions is 180°.

* * * * *